United States Patent [19]

Wee et al.

[11] Patent Number: 4,871,391
[45] Date of Patent: Oct. 3, 1989

[54] HERBICIDAL 5-SUBSTITUTED-2-4-IMIDAZOLIDINEDIONES

[75] Inventors: Siok H. H. Wee, Berkeley; Michael P. Prisbylla, Richmond, both of Calif.

[73] Assignee: ICI Americas Inc., Wilmington, Del.

[21] Appl. No.: 220,298

[22] Filed: Jul. 18, 1988

[51] Int. Cl.$^4$ .................. A01N 43/50; C07D 233/86; C07D 233/72
[52] U.S. Cl. ......................................... 71/92; 548/311
[58] Field of Search ............................. 548/311; 71/92

[56] References Cited
PUBLICATIONS

*Chemical Abstracts,* 97: 14753n(1982)[JPN. Kokai Tokyo Koho JP 81,153,343, 11/27/81].

*Primary Examiner*—Richard A. Schwartz
*Attorney, Agent, or Firm*—Harry A. Pacini

[57] ABSTRACT

5-Substituted 2,4-imidazolidinediones having the formula

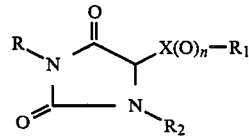

wherein
R is alkyl, phenyl or phenyl substituterd with alkyl, alkoxy, halo, haloalkyl, nitro or combinations thereof;
$R_1$ is alkyl, cycloalkyl, carboalkyl, alkylcarboalkyl, carboalkoxy, thionocarboalkoxy, phenyl, phenalkyl, phenyl substituted with alkyl, alkoxy, haloalkyl, nitro or combinations thereof; benzyl or benzyl substituted with one or more halo; pyridine, pyridine substituted with halo; or heterocycle such as, but not limited to, pyrimidine, pyrimidine substituted with halo, alkyl or combinations thereof; imidazole, methylimidazole; benzimidazole; triazole, triazole substituted with haloalkyl, alkyl or combinations thereof; triazoline, triazoline, triazoline substituted with haloalkyl, alkyl, or combinations thereof; thiazole or thiazole substituted with phenyl;
$R_2$ is lower alkyl, phenyl or phenyl substituted with one or more alkyl, halo or haloalkyl;
X is sulfur, oxygen or nitrogen; and
n is an integer from 0 to 2, inclusive,
are useful herbicidal agents. Also included is a process of making certain intermediates of the invention.

60 Claims, No Drawings

HERBICIDAL 5-SUBSTITUTED-2-4-IMIDAZOLIDINEDIONES

BACKGROUND OF THE INVENTION

This invention relates to herbicides and, more particularly, to certain novel substituted 5-nitrogen, oxygen or sulfur 2,4-imidazolidinediones and the process for the preparation of certain intermediates of these compounds.

DESCRIPTION OF THE INVENTION

This invention relates to novel herbicidal compounds and a process for preparation of certain intermediates of these compounds having the formula

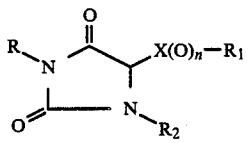

wherein
R is alkyl, phenyl or phenyl substituted with alkyl, alkoxy, halo, haloalkyl, nitro or combinations thereof;
$R_1$ is alkyl, cycloalkyl, carboalkyl, alkylcarboalkyl, carboalkoxy, thionocarboalkoxy, phenyl, phenalkyl, phenyl substituted with alkyl, alkoxy, halo, haloalkyl, nitro or combinations thereof; benzyl or benzyl substituted with one or more halo; pyridine, pyridine substituted with halo; or heterocycle such as, but not limited to, pyrimidine, pyrimidine substituted with halo, alkyl or combinations thereof; imidazole, methylimidazole; benzimidazole; triazole, triazole substituted with haloalkyl, alkyl or combinations thereof; triazoline, triazoline substituted with haloalkyl, alkyl, or combinations thereof; thiazole or thiazole substituted with phenyl;
$R_2$ is lower alkyl, phenyl or phenyl substituted with one or more alkyl, halo or haloalkyl;
X is sulfur, oxygen or nitrogen; and
n is an integer from 0 to 2, inclusive.

The term "cycloalkyl" includes saturated cyclic hydrocarbyl moieties and includes such moieties having from 3 to 6 carbon atoms. The term "alkyl" includes both straight and branched chain saturated acyclic hydrocarbyl moieties and includes such moieties having from 1 to 10 carbon atoms such as methyl, ethyl, n-propyl, isopropyl, n-butyl, sec-butyl, isobutyl and tert-butyl, as well as the 6 pentyls and 16 hexyls. Where the alkyl group is used to connect moieties such as phenyl, halogen, sulfonyl or pyridyl, the term "lower alkyl" includes such hydrocarbyl moieties having from 1–3 carbon atoms such as methyl, ethyl and propyl. The term "alkoxy" includes both straight and branched saturated acyclic hydrocarbyl moieties which contain an oxygen in the chain and includes such moieties having from 1 to 4 carbon atoms, for example methoxy, ethoxy, n-propoxy, isopropoxy, n-butoxy, sec-butoxy, isobutoxy and t-butoxy. The term "halo" includes fluorine, chlorine, bromine or iodine as mono-, di-, tri- and mixed halogen substitutions.

The process of this invention embodies compounds having the formula

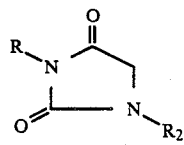

wherein R is lower alkyl, alkoxy, halo, haloalkyl, nitro or combinations thereof; $R_2$ is phenyl, phenyl substituted with alkyl, alkoxy, haloalkyl, nitro or combinations thereof.

The herbicidal 5-unsubstituted-2,4-imidazolidinedione intermediates of this process can be made by reacting an N-phenyl-2,2,2-trihaloacetanilide with an N-alkyl-2-haloacetamide in the presence of an inorganic base and a catalyst or a metal hydride base and a suitable solvent. The product of this reaction can be isolated, then purified by suitable means such as chromatography through silica gel with a suitable solvent or mixture of solvents. The intermediates of this reaction can then be further reacted via standard procedures to produce the 5-substituted-2,4-imidazolidinedione herbicides.

The preferred bases of this reaction include potassium carbonate, sodium carbonate, sodium hydride, trisodium phosphate or tripotassium phosphate, more preferably potassium carbonate and sodium hydride. A preferred catalyst is potassium iodide. Preferred solvents of this reaction are acetone, methylethyl ketone, methylisopropyl ketone, dimethylformamide, benzene, toluene, diethyl ether and tetrahydrofuran.

Where the preferred base is potassium carbonate, a catalytic amount of potassium iodide is used in amounts ranging from about 0.1 to about 10% by weight based on the N-phenyl-2,2,2-trihaloacetanilide and the preferred solvents are acetone or methylethyl ketone. Where the preferred base is sodium hydride, the preferred solvents are dimethylformamide or tetrahydrofuran.

The preferred temperatures of this reaction are from about 50 to about 120° C. The preferred temperature when utilizing an inorganic base is about 80° C. The preferred temperature when utilizing a metal hydride is about 70° C.

This reaction can be run at subatmospheric, atmospheric or superatmospheric pressure, preferably at atmospheric pressure.

The compounds of this invention have been found to be active herbicides in possessing herbicidal activity against various species of weeds. In the broadest sense, the term "weeds" refers to plants which grow in locations in which they are not desired.

This invention also therefore relates to a method for controlling undesirable vegetation, comprising applying to a locus where control of such vegetation is desired an herbicidally effective amount of a compound as described herein, and also relates to herbicidal compositions of matter comprising an herbicidally effective amount of a compound as described herein, together with an inert diluent or carrier suitable for use with herbicides.

As used herein the term "herbicide" refers to compounds which adversely control or modify the growth of plants, particularly of undesirable plants. By the term "herbicidally effective amount" is meant an amount of compound which causes an adverse controlling or modifying effect on the growth of plants. The term "plants" is meant to include germinant seeds, emerging seedlings, and established vegetation, including roots and above-ground portions. Such adverse modifying and controlling effects may include all deviations from natural development.

The compounds of this invention may be prepared as shown in the following Schematics 1–8. The process of this invention can be characterized by the following Schematic 5.

Schematic 1 depicts the preparation of the 5-thio-substituted-3-aryl-2,4-dioxo-1-alkylimidazoline by reaction of a 5-hydroxy-substituted-2,4-imidazolidinedione with a tertiary amine, a sulfonyl chloride and then the mercaptan of choice.

Schematic 2 depicts the preparation of the 3-aryl-2,4-dioxo-1-alkylimidazolidine by reaction of a urea with hydrochloric acid.

Schematic 3 depicts the preparation of the 1-alkyl-2,4-dioxo-3-arylimidazolidine by reaction of a chloroacetanilide with an amine to yield a sarcosine anilide.

Schematic 4 depicts the preparation of a 1-alkyl-2,4-dioxo-3-arylimidazolidine by reaction of an aryl sarcosine anilide with carbonyldiimidazole.

Schematics 5a and 5b depict the preparation of a 1-aryl-2,4-dioxo-3-alkylimidazolidine by reaction of an N-aryl-2,2,2-trihaloacetanilide with an N-alkyl-2-haloacetamide, an inorganic base and catalyst or a metal hydride base.

Schematic 6 depicts the preparation of (a) a 5-oxy-substituted-3-aryl-2,4-dioxo-1-alkylimidazoline by reaction of a 5-methanesulfonyloxy substituted-3-aryl-2,4-dioxo-1-alkylimidazolone with a phenol and (b) a 5-anilino substituted-3-aryl-2,4-dioxo-1-alkylimidazolidine with an aniline.

Schematic 7 depicts the preparation of a 5-pyrimdyloxy-substituted-3-aryl-2,4-dioxo-1-alkylimdazolidine.

Schematic 8 depicts preparation of the sulfone from the 5-thio-substituted-1-aryl-2,4-dioxo-3-alkylimidazolidine and an organic peroxide.

Schematic 9 depicts (a) bromination at the 5-position of the imidazolidine and (b) condensation with the mercaptan.

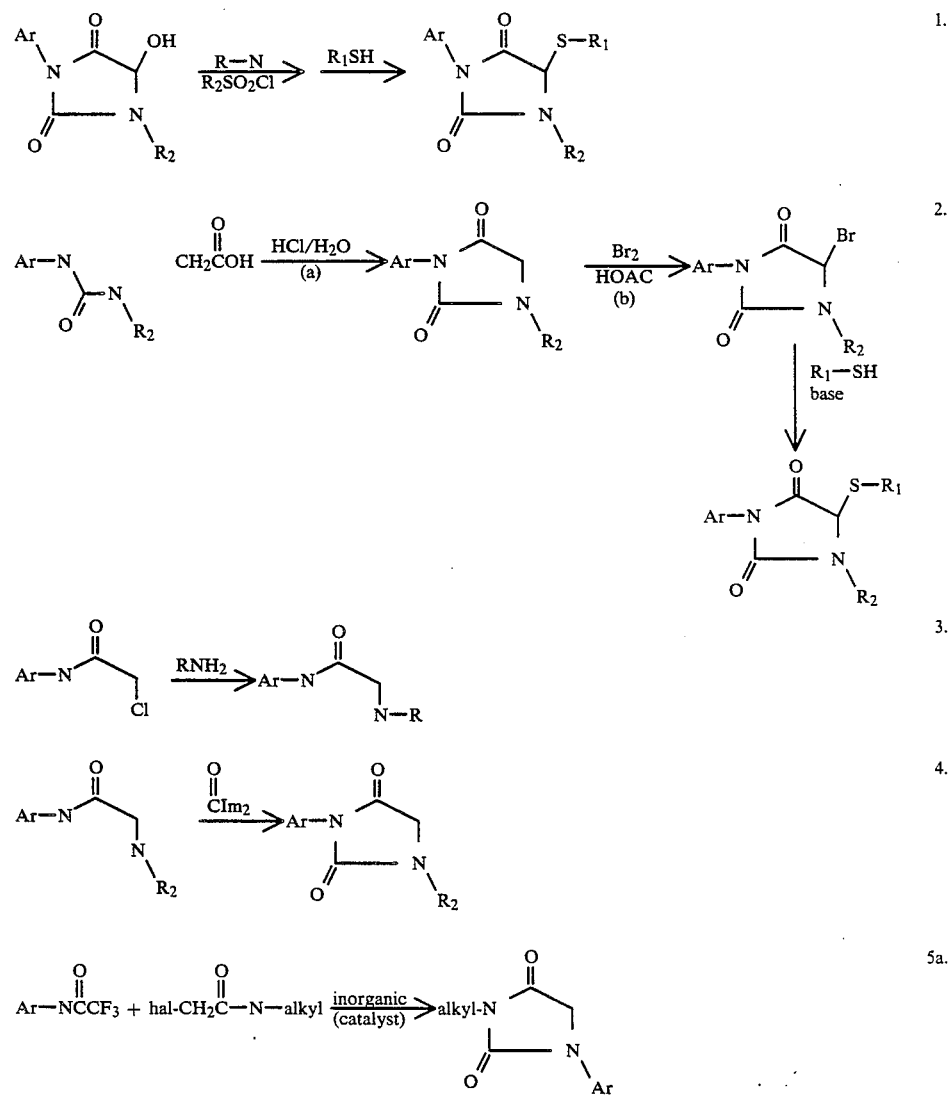

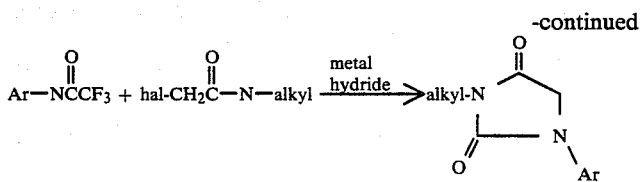

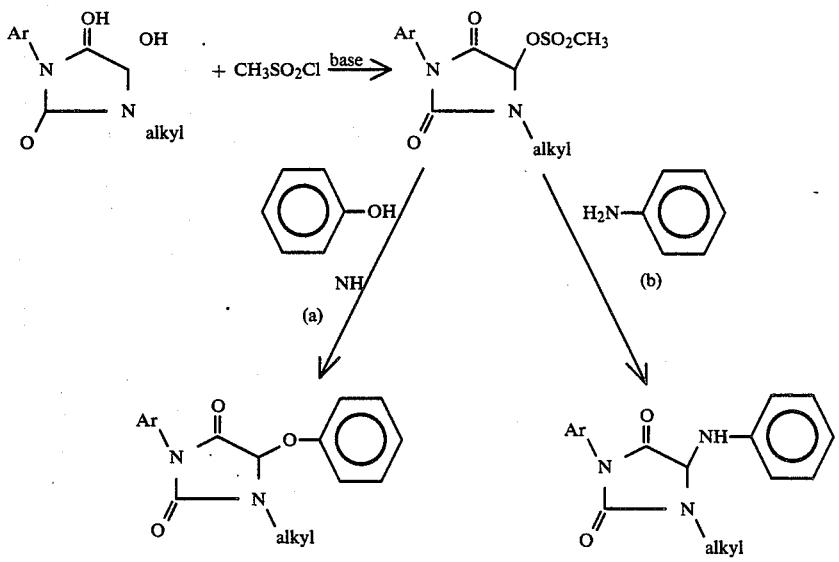

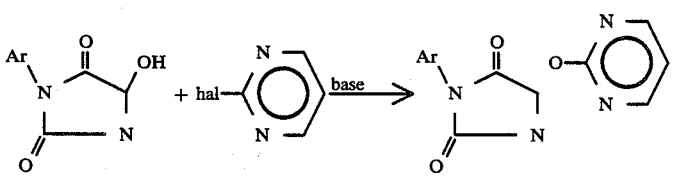

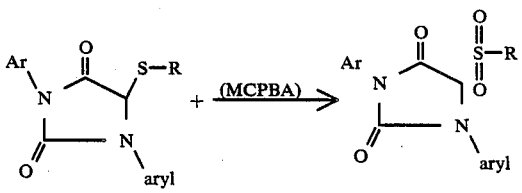

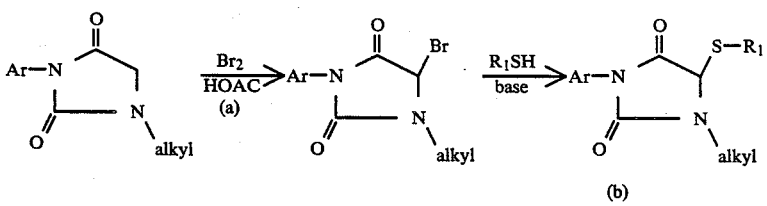

The following are examples of the preparation of compounds and the process of this invention, the structures of which were confirmed by infrared, nuclear magnetic resonance and mass spectroscopy.

EXAMPLE 1

Preparation of 5-(2-Chlorophenyl)thio-3-(2-fluoro)phenyl-2,4-dioxo-1-methylimidazolidine To a solution of 25 milliliter (ml) methylene chloride and 2.2 grams (g) (10 mmol) 5-hydroxy-3-(2-fluoro)phenyl-2,4-dioxo-1-methylimidazolidine cooled in an ice bath was added 1.1 g triethylamine (11 mmol) and 1.3 g (11 mmol) methanesulfonyl chloride. The mixture was left to stir in the ice bath for 2 hours. 2-Chloro-thiophenol (1.6 g, 11 mmol) was added and the mixture was left to stir overnight under reflux. The mixture was worked up by removal of the solvent by a rotary evaporator, chromatography through a silica gel column using methylene chloride-hexane mixture (1:2 then 1:1) to obtain the desired product, 1.8 g (51% yield) of product, melting point 95°–98° C.

EXAMPLE 2

Preparation of 3-(2-Fluoro)phenyl-2,4-dioxo-1-methylimidazolidine

A mixture of N-(2-fluoro)phenyl-N'-methyl-N'-(carboxy)methylurea (20.0 g, 90 mmol) in 6M hydrochloric acid (100 ml) was heated under reflux for 30 minutes. The mixture was cooled in an ice bath. The white solid product was obtained by filtration and washed with water. After drying, 18.5 g (99% yield) of the product was obtained, melting point 105°–107° C.

EXAMPLE 3

Preparation of N-(2-Fluoro)phenyl sarcosine anilide

To an ethanolic (70 ml) solution of N-(2-fluoro)phenyl-2-chloroacetanilide (21.6 g, 0.11 mol) was added 40% aqueous methylamine (70 ml) and stirred at room temperature overnight. The mixture was concentrated in a rotary evaporator. The product was extracted into ethyl ether (200 ml) and the organic layer dried with magnesium sulfate and concentrated. The crude product was passed through a short column of silica gel using 1:1 methylene chloride-hexane as the eluent. The product obtained was a yellow oil weighing 18.2 g (88%).

EXAMPLE 4

Preparation of 3-(2-Fluoro)phenyl-2,4-dioxo-1-methylimidazolidine

To a benzene (25 ml) solution of N-(2-fluoro)phenyl sarcosine anilide (2.0 g, 10 mmol) was added 1,1'-carbonyldiimidazole (2.0 g, 12 mmol). The mixture was heated under reflux overnight, diluted with ethyl acetate (25 ml) and washed with water (40 ml). The organic layer was dried with magnesium sulfate and concentrated on a rotary evaporator to give 2.2 g (96%) of product.

EXAMPLE 5a

Preparation of 1-(2-Fluoro)phenyl-2,4-dioxo-3-methylimidazolidine

A mixture of N-(2-fluoro)phenyl-2,2,2-trifluoroacetanilide (10.7 g, 52 mmol), potassium carbonate (7.2 g, 52 mmol), N-methyl-2-chloroacetamide (7.2 g, 67 mmol) and potassium iodide (2.0 g, catalytic) in methyl ethyl ketone (200 ml) was heated under reflux for 48 hours. The solvent was removed on a rotary evaporator and the residue taken up in ethyl acetate, washed with water, dried with magnesium sulfate and concentrated on a rotary evaporator. The product was purified using silica gel for chromatography (19:1 to 1:1) hexane-ethyl acetate as eluent, and 7.0 g (69% yield) of product was obtained with a melting point of 128°–131° C.

EXAMPLE 5b

Preparation of 1-(2-Fluorophenyl)-3-methylimidazolidin-2,4-dione

To a THF (50 ml) suspension of sodium hydride (1.4 g, 0.06 mole) was added 2-fluorotrifluoroacetanilide (10.0 g, 0.05 mole). The mixture was stirred at room temperature for 30 minutes then N-methyl-2-chloroacetamide (6.5 g, 0.06 mole) and potassium iodide (~1.5 g, catalytic amount) were added. After heating under reflux overnight, the reaction was allowed to cool to room temperature. The THF solvent was removed in a rotary evaporator. Ethyl acetate (100 ml) was added and the mixture washed with water (100 ml). The mixture was dried with magnesium sulfate and concentrated in a rotary evaporator. The product was purified through chromatography on silica gel using a solvent mixture of dichloromethane and hexane. Thin layer chromatography (1:1 hexane-ethyl acetate) of the product gave an Rf of 0.51. The white solid obtained yields 50% of the anticipated product.

EXAMPLE 6a

Preparation of 5-(4-Chloro)phenoxy-3-(3-chloro)phenyl-2,4-dioxo-1-methylimidazolidine To a solution of 5-hydroxy-3-(3-chloro)phenyl-2,4-dioxo-1-methylimidazolidine (5.4 g, 22 mmol) in tetrahydrofuran (25 ml), cooled in an ice bath, was added methanesulfonyl chloride (2.6 g, 22 mmol) and triethylamine (2.3 g, 22 mmol). The mixture was stirred in the ice bath for 2 hours. In a separate flask, 4-chlorophenol (2.9 g, 22 mmol) was added to sodium hydride (0.54 g, 22 mmol) suspended in tetrahydrofuran (10 ml) and the mixture was also stirred for 2 hours at room temperature. The phenoxide was transferred by syringe to the cold mesylate solution and stirred overnight at room temperature. The solvent was removed on a rotary evaporator. The residue was taken up in 1:1 methylene chloride-hexane and chromatographed through silica gel to give 5.8 g (73% yield) of pure product.

EXAMPLE 6b

Preparation of 5-(2-Chloro)anilino-3-(3-chloro)phenyl-2,4-dioxo-1-methylimidazolidine To a solution of 5-hydroxy-3-(3-chloro)phenyl-2,4-dioxo-1-methylimidazolidine (3.6 g, 15 mmol) in methylene chloride (20 ml) cooled in an ice bath, was added triethylamine (1.5 g, 15 mmol) and methanesulfonyl chloride (1.7 g, 15 mmol). The mixture was allowed to stir for 2 hours in the ice bath, then 2-chloroaniline (1.4 g, 15 mmol) was added and stirred at room temperature for 2 hours. The reaction was worked up by diluting with hexane (20 ml) and filtered through florisil. The product was obtained by eluting with 3:1 methylene chloride-hexane to give 2.1 g of impure product which was further purified by chromatotron.

EXAMPLE 7

Preparation of 5-[2-(4,6-dimethyl)pyrimidinyl]oxy-3-(4-chloro)phenyl-2,4-dioxo-1-methylimidazolidine To a suspension of sodium hydride (0.3 g, 12 mmol) in DMF (20 ml) was added 5-hydroxy-3-(3-chloro)phenyl-2,4-dioxo-1-methylimidazolidine (3.0 g, 12 mmol). The mixture was stirred for 30 minutes at room temperature, then 2-chloro-4,6-dimethylpyrimidine (1.8 g, 12 mmol) was added. The reaction was heated under reflux overnight, worked up by pouring into water (20 ml) and extracting with ethyl acetate. The organic layer was washed with water (twice, 20 ml) and brine, and dried with magnesium sulfate. Hexane (30 ml) was added and the resulting mixture was filtered through a pad of silica gel. Further clean up with chromatotron using 3:1 hexane-ethyl acetate resulted in pure product (0.7 g, 15% yield).

EXAMPLE 8

Preparation of 5-(4-Fluorophenylsulfonyl)-3-(3-chlorophenyl)-1-methylimidazolidine-2,4-dione Meta-Chloroperbenzoic acid (0.91 g, 5.3 mmol) was added portionwise (as a solid) to a solution of the sulfide (838 mg, 2.239 mmol) in chloroform (25 ml) at 0° C., allowed to warm to room temperature and stirred overnight. The solution was diluted with $CH_2Cl_2$ and washed with 10% sodium thiosulfate, sodium bicarbonate (saturated), brine (saturated), dried over magnesium sulfate, filtered and concentrated to give 0.90 g of a yellow solid, melting point 170°–173° C.

EXAMPLE 9

Preparation of 5-(2-Chlorophenyl)thio-3-(2-fluoro)phenyl-2,4-dioxo-1-methylimidazolidine To a solution of 3-(2-fluoro)phenyl-2,4-dioxo-1-methylimidazolidine (20.0 g, 96 mmol) and bromine (16.8 g, 105 mmol) in glacial acetic acid (100 ml) was heated in an oil bath with temperature of 95° C. for 2 hours until the bromine color faded away. The mixture was allowed to cool to room temperature and concentrated by a rotary evaporation. Toluene (25 ml) was added and the mixture was reconcentrated to remove the last traces of acetic acid; this procedure was repeated with another 25 ml of toluene. The 5-bromo-(2-chloro)phenyl-3-(2-fluorophenyl-2,4-dioxo-1-methylimidazolidine obtained was dissolved in methylene chloride (300 ml) and the solution cooled in an ice bath. To the mixture was added 2-chlorothiophenol (13.8 g, 96 mmol) followed by pyridine (11.3 g, 144 mmol). The mixture was left to stir at room temperature overnight, then washed with water, dried with magnesium sulfate and concentrated on a rotary evaporator. The crude product was triturated with 5:1 hexane-ethyl acetate to give a 23 g (68% yield) of the white solid product.

The following Table I illustrates embodiments of this invention. Structures of the indicated compounds were confirmed by spectral analysis.

TABLE I

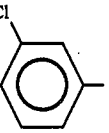

| Cmpd. No. | R | $R_1$ | $R_2$ | X | n | $n_D^{30}$ or m.p. °C. or Constant |
|---|---|---|---|---|---|---|
| 1 | Cl—C6H4— 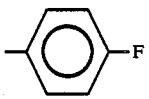 | —C6H4—F 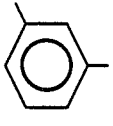 | —CH3 | S | 0 | 104–108 |
| 2 | Cl—C6H4— 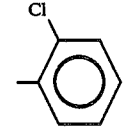 | Cl—C6H4— 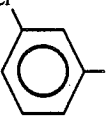 | —CH3 | S | 0 | 1.6272 |
| 3 | Cl—C6H4— 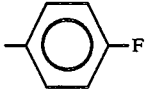 | —C6H4—F 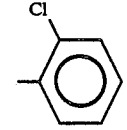 | —CH3 | S | 2 | 170–173 |
| 4 | —CH3 | Cl—C6H4— 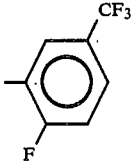 | —C6H3(CF3)(F) 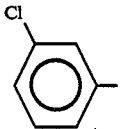 | S | 0 | 110–113 |
| 5 | Cl—C6H4— 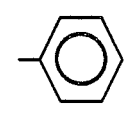 | —C6H5 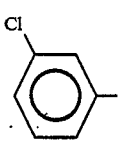 | —CH3 | S | 0 | thick oil |
| 6 | Cl—C6H4— 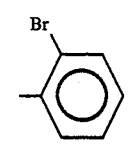 | Br | —CH3 | S | 0 | thick oil |

TABLE I-continued $$\underset{O}{\overset{R}{\underset{N}{\bigvee}}}\overset{O}{\underset{N_{R_2}}{\bigvee}}X(O)_n-R_1$$

| Cmpd. No. | R | $R_1$ | $R_2$ | X | n | $n_D^{30}$ or m.p. °C. or Constant |
|---|---|---|---|---|---|---|
| 7 | 3-Cl-C₆H₄ | 2-CH₃-C₆H₄ | —CH₃ | S | 0 | 110–112 |
| 8 | 3-Cl-C₆H₄ | 2-OCH₃-C₆H₄ | —CH₃ | S | 0 | 80–83 |
| 9 | 3-Cl-C₆H₄ | 4-Cl-C₆H₄ | —CH₃ | S | 0 | thick oil |
| 10 | 3-Cl-C₆H₄ | 4-CH₃-C₆H₄ | —CH₃ | S | 0 | thick oil |
| 11 | 3-Cl-C₆H₄ | 2,6-Cl₂-C₆H₃ | —CH₃ | S | 0 | thick oil |
| 12 | 3-Cl-C₆H₄ | —C(CH₃)₃ | —CH₃ | S | 0 | 103–108 |
| 13 | 3-CF₃-C₆H₄ | 2-Cl-C₆H₄ | | | | |
| 14 | C₆H₅ | 2-Cl-C₆H₄ | —CH₃ | S | 0 | thick oil |
| 15 | 3,4-Cl₂-C₆H₃ | 2-Cl-C₆H₄ | —CH₃ | S | 0 | 70–74 |

TABLE I-continued
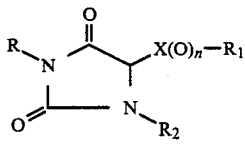
| Cmpd. No. | R | R₁ | R₂ | X | n | $n_D^{30}$ or m.p. °C. or Constant |
|---|---|---|---|---|---|---|
| 16 | 2-F-phenyl | 4-NO₂-phenyl | —CH₃ | S | 0 | semi-solid |
| 17 | phenyl | 2-Cl-phenyl | —CH₃ | N | 0 | 101–110 |
| 18 | 3-Cl-phenyl | —CH₂COCH₃ | —CH₃ | S | 0 | glassy paste |
| 19 | 3-Cl-phenyl | 2-Cl-phenyl | —CH₃ | N | 0 | 103–125 |
| 20 | 3-Cl-phenyl | pyrimidinyl | —CH₃ | S | 0 | 140–145 |
| 21 | 3-Cl-phenyl | 2-pyridyl | —CH₃ | S | 0 | 148–153 |
| 22 | 3-Cl-phenyl | 1-methylimidazolyl | —CH₃ | S | 0 | thick oil |
| 23 | 3-Cl-phenyl | benzimidazolyl | —CH₃ | S | 0 | 85–92 |
| 24 | 3-Cl-phenyl | —CH₂-phenyl | —CH₃ | S | 0 | thick oil |

TABLE I-continued $$R-N(-)-C(=O)-CH(X(O)_n-R_1)-N(R_2)-C(=O)-$$
(cyclic structure with R on one N, R₂ on other N, and CH bearing X(O)ₙ—R₁ substituent)

| Cmpd. No. | R | R₁ | R₂ | X | n | n$_D^{30}$ or m.p. °C. or Constant |
|---|---|---|---|---|---|---|
| 25 | 4-CH₃-phenyl | 2-Cl-phenyl | —CH₃ | S | 0 | 75–80 |
| 26 | 4-Cl-phenyl | 2-Cl-phenyl | —CH₃ | S | 0 | 112–114 |
| 27 | 3-Cl-phenyl | 5-Cl-pyrimidin-2-yl | —CH₃ | O | 0 | yellow oil |
| 28 | 3-Cl-phenyl | 2,3,5,6-tetrachloropyridin-4-yl | —CH₃ | S | 0 | 54–65 |
| 29 | 3-Cl-phenyl | —CH₂—(4-Cl-phenyl) | —CH₃ | S | 0 | 102–106 |
| 30 | 3-Cl-phenyl | —CH₂—(3,4-diCl-phenyl) | —CH₃ | S | 0 | 88–90 |
| 31 | 4-CH₃O-phenyl | 2-Cl-phenyl | —CH₃ | S | 0 | 101–103 |
| 32 | 3-Cl-phenyl | 2-Cl-phenyl | —CH₃ | O | 0 | 111–116 |
| 33 | 3-Cl-phenyl | —CH₂—(2-Cl-phenyl) | —CH₃ | S | 0 | 100–104 |

TABLE I-continued

Structure: R-N(ring)-C(=O)-CH(X(O)n-R1)-N(R2), with C=O in ring

| Cmpd. No. | R | R₁ | R₂ | X | n | $n_D^{30}$ or m.p. °C. or Constant |
|---|---|---|---|---|---|---|
| 34 | 3-Cl-phenyl | 2-F-phenyl | —CH₃ | S | 0 | thick oil |
| 35 | 3-Cl-phenyl | 4-OCH₃-phenyl | —CH₃ | S | 0 | thick oil |
| 36 | 3-Cl-phenyl | 3,4-diCl-phenyl | —CH₃ | S | 0 | thick oil |
| 37 | 3-Cl-phenyl | —C(CH₃)₂—CH₂—C(CH₃)₃ | —CH₃ | S | 0 | 83–85 |
| 38 | 3-Cl-phenyl | —(CH₂)₇CH₃ | —CH₃ | S | 0 | 80–81 |
| 39 | 3-Cl-phenyl | —(CH₂)₈CH₃ | —CH₃ | S | 0 | 80–82 |
| 40 | 3-Cl-phenyl | 4,6-dimethylpyrimidin-2-yl | —CH₃ | S | 0 | 90–100 |
| 41 | 3-Cl-phenyl | 4-NO₂-phenyl | —CH₃ | S | 0 | semi-solid |
| 42 | 3-Cl-phenyl | cyclohexyl | —CH₃ | S | 0 | 44–48 |

TABLE I-continued
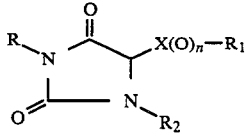
| Cmpd. No. | R | R₁ | R₂ | X | n | $n_D^{30}$ or m.p. °C. or Constant |
|---|---|---|---|---|---|---|
| 43 | 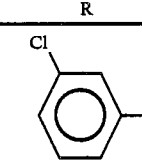 3-Cl-phenyl | 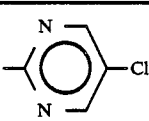 5-Cl-pyrimidin-2-yl | —CH₃ | S | 0 | 145–147 |
| 44 | 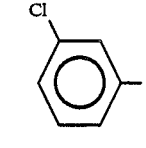 3-Cl-phenyl | —CH₂CH₂COCH₃ | —CH₃ | S | 0 | thick oil |
| 45 | 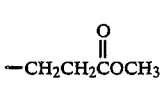 3,4-di-Cl-phenyl | 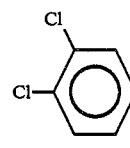 4-Br-phenyl | —CH₃ | S | 0 | 94–109 |
| 46 | 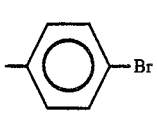 3,4-di-Cl-phenyl | 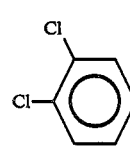 4-pyridyl | —CH₃ | S | 0 | 169–175 |
| 47 | 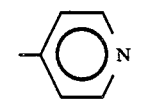 4-Cl-phenyl | 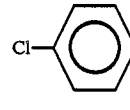 4-Cl-phenyl | —CH₃ | S | 0 | 102–119 |
| 48 | 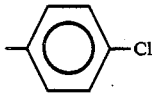 3,4-di-Cl-phenyl | 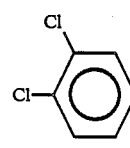 1,2,4-triazol-3-yl | —CH₃ | S | 0 | 150–170 |
| 49 | 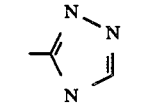 3,4-di-Cl-phenyl | 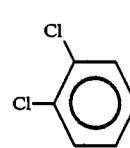 1-methyl-5-CF₃-1,2,4-triazol-3-yl | —CH₃ | S | 0 | 105–129 |
| 50 | 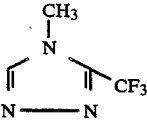 4-Cl-phenyl | 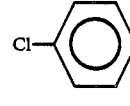 phenyl | —CH₃ | S | 0 | thick oil |
| 51 | 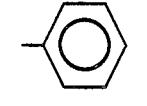 4-Cl-phenyl | —CH₂—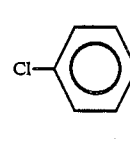 2-Cl-benzyl | —CH₃ | S | 0 | 115–117 |
| 52 | 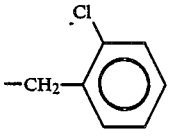 4-Cl-phenyl | —CH₂CH₂CH₃ | —CH₃ | S | 0 | 115–117 |

TABLE I-continued $$\begin{array}{c}\text{R}\\ \diagdown\\ \text{N}\end{array}\begin{array}{c}\text{O}\\ \parallel\\ \end{array}\begin{array}{c}\text{X(O)}_n-\text{R}_1\\ \diagup\\ \text{CH}\\ \diagdown\\ \text{N}-\text{R}_2\end{array}$$

| Cmpd. No. | R | R₁ | R₂ | X | n | $n_D^{30}$ or m.p. °C. or Constant |
|---|---|---|---|---|---|---|
| 53 | 4-Cl-C₆H₄- | -CH(CH₃)₂ | -CH₃ | S | 0 | 75-80 |
| 54 | 4-Cl-C₆H₄- | -(CH₂)₃CH₃ | -CH₃ | S | 0 | 100-103 |
| 55 | 4-Cl-C₆H₄- | 4-phenyl-thiazol-2-yl | -CH₃ | S | 0 | 140-144 |
| 56 | 4-Cl-C₆H₄- | 3-Cl-C₆H₄- | -CH₃ | S | 0 | 112-114 |
| 57 | C₆H₅- | -CH₂-C(O)OCH₃ | -CH₃ | S | 0 | thick oil |
| 58 | 4-Cl-C₆H₄- | pyrimidin-2-yl | -CH₃ | S | 0 | 146-153 |
| 59 | 4-Cl-C₆H₄- | pyridin-2-yl | -CH₃ | S | 0 | 137-145 |
| 60 | 4-Cl-C₆H₄- | 4,6-dimethylpyrimidin-2-yl | -CH₃ | S | 0 | 163-168 |
| 61 | 4-Cl-C₆H₄- | 4-Br-C₆H₄- | -CH₃ | S | 0 | 110-114 |
| 62 | C₆H₅- | -CH₂-(2-Cl-C₆H₄) | -CH₃ | S | 0 | 120-123 |

TABLE I-continued
$$\underset{O}{\overset{R}{\underset{\|}{N}}}\underset{N}{\overset{O}{\underset{\|}{\bigvee}}}\underset{R_2}{\overset{X(O)_n-R_1}{\bigvee}}$$
| Cmpd. No. | R | R₁ | R₂ | X | n | $n_D^{30}$ or m.p. °C. or Constant |
|---|---|---|---|---|---|---|
| 63 | 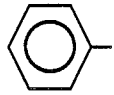 | 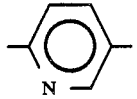 | —CH₃ | S | 0 | 120–130 |
| 64 | 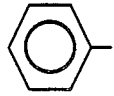 | 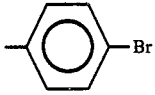 | —CH₃ | S | 0 | 118–120 |
| 65 | 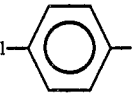 | 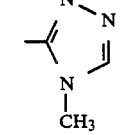 | —CH₃ | S | 0 | thick oil |
| 66 | 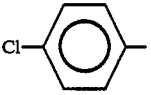 |  | —CH₃ | S | 0 | 115–117 |
| 67 | 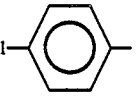 | 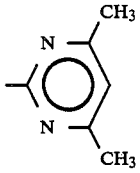 | —CH₃ | O | 0 | 156–159 |
| 68 | 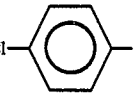 | 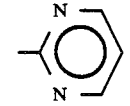 | —C₂H₅ | S | 0 | 150–154 |
| 69 | 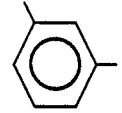 | 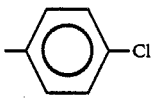 | —CH₃ | O | 0 | thick oil |
| 70 | 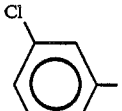 |  | —CH₃ | S | 0 | 82–85 |
| 71 | 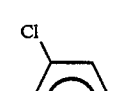 | 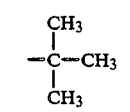 | —CH₃ | S | 0 | 134–136 |
| 72 | 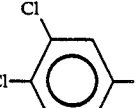 |  | —CH₃ | S | 0 | 93–96 |

TABLE I-continued

[Structure: R-N(C=O)-CH(X(O)n-R1)-N(R2)-C(=O) hydantoin-type ring]

| Cmpd. No. | R | R₁ | R₂ | X | n | $n_D^{30}$ or m.p. °C. or Constant |
|---|---|---|---|---|---|---|
| 73 | 3,4-dichlorophenyl | —CH₂CH₂COCH₃ | —CH₃ | S | 0 | thick oil |
| 74 | 2-fluorophenyl | 2,3,5,6-tetrachloropyridin-4-yl | —CH₃ | S | 0 | 181–184 |
| 75 | 3,4-dichlorophenyl | 2,3,5,6-tetrachloropyridin-4-yl | —CH₃ | S | 0 | 73–75 |
| 76 | 2-fluorophenyl | 2-chlorophenyl | —CH₃ | S | 0 | 95–98 |
| 77 | 2-fluorophenyl | —CH₂COCH₃ | —CH₃ | S | 0 | 103–105 |
| 78 | 2-fluorophenyl | —C(CH₃)₃ | —CH₃ | S | 0 | 104–106 |
| 79 | 2-fluorophenyl | 2-bromophenyl | —CH₃ | S | 0 | 99–103 |
| 80 | 3,4-dichlorophenyl | 2-bromophenyl | —CH₃ | S | 0 | 59–62 |
| 81 | 2-fluorophenyl | pyridin-2-yl | —CH₃ | S | 0 | 135–137 |

TABLE I-continued
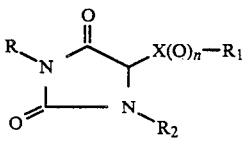
| Cmpd. No. | R | R₁ | R₂ | X | n | $n_D^{30}$ or m.p. °C. or Constant |
|---|---|---|---|---|---|---|
| 82 | 2-F-phenyl | —CH₂CH₂COCH₃ | —CH₃ | S | 0 | thick oil |
| 83 | 2,4-di-F-phenyl | 2-Cl-phenyl | —CH₃ | S | 0 | thick oil |
| 84 | 4-F-phenyl | 2-Cl-phenyl | —CH₃ | S | 0 | 80–83 |
| 85 | 4-F-phenyl | pyrimidinyl | —CH₃ | S | 0 | 139–141 |
| 86 | 4-F-phenyl | pyridinyl | —CH₃ | S | 0 | 113–115 |
| 87 | 4-F-phenyl | —C(CH₃)₃ | —CH₃ | S | 0 | 132–134 |
| 88 | 3,4-di-Cl-phenyl | pyridinyl | —CH₃ | S | 0 | 140–142 |
| 89 | 2,4-di-F-phenyl | —C(CH₃)₃ | —CH₃ | S | 0 | thick oil |
| 90 | —CH₃ | pyrimidinyl | 3,4-di-Cl-phenyl | S | 0 | 194–195 |

TABLE I-continued

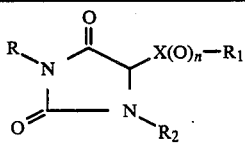

| Cmpd. No. | R | R₁ | R₂ | X | n | $n_D^{30}$ or m.p. °C. or Constant |
|---|---|---|---|---|---|---|
| 91 | —CH₃ | 2,4-difluorophenyl | 3-chlorophenyl | S | 0 | 93–95 |
| 92 | 4-fluorophenyl | —CH₂COCH₃ | —CH₃ | S | 0 | 78–80 |
| 93 | 2,5-difluorophenyl | 2-bromophenyl | —CH₃ | S | 0 | semi-solid |
| 94 | 2,5-difluorophenyl | —CH₂COCH₃ | —CH₃ | S | 0 | 80–83 |
| 95 | phenyl | pyrimidin-2-yl | —CH₃ | S | 0 | 165–166 |
| 96 | 4-chlorophenyl | 1,2,4-triazol-3-yl | —CH₃ | S | 0 | 90–93 |
| 97 | 2,4-difluorophenyl | 5-chloropyrimidin-2-yl | —CH₃ | O | 0 | 150–151 |
| 98 | 2-fluorophenyl | 2-chlorobenzyl | —CH₃ | S | 0 | 108–110 |
| 99 | 2,4-difluorophenyl | 4-chlorophenyl | —CH₃ | S | 0 | 134–137 |

TABLE I-continued

R-N(C=O)(C=O)-N(R2)-CH-X(O)n-R1

| Cmpd. No. | R | R₁ | R₂ | X | n | $n_D^{30}$ or m.p. °C. or Constant |
|---|---|---|---|---|---|---|
| 100 | —CH₃ | pyrimidin-2-yl | 2-F-phenyl | S | 0 | 200–202 |
| 101 | 2-F-phenyl | pyrimidin-2-yl | —CH₃ | S | 0 | 140–143 |
| 102 | 2-F-phenyl | 4-Cl-phenyl | —CH₃ | S | 0 | 120–124 |
| 103 | 3,4-diCl-phenyl | pyrimidin-2-yl | —CH₃ | S | 0 | 164–168 |
| 104 | 3-CF₃-phenyl | pyrimidin-2-yl | —CH₃ | S | 0 | 165–167 |
| 105 | 3-CF₃-phenyl | —CH₂COCH₃ | —CH₃ | S | 0 | 95–97 |
| 106 | 3-CF₃-phenyl | —C(CH₃)₃ | —CH₃ | S | 0 | 132–133 |
| 107 | 3-CF₃-phenyl | 2-Br-phenyl | —CH₃ | S | 0 | 88–90 |
| 108 | 2-F-phenyl | 2-(CH(CH₃)₂)-phenyl | —CH₃ | S | 0 | 90–92 |

TABLE I-continued

R-N(C=O)-CH(X(O)n-R1)-N(C=O)-R2 (hydantoin-like structure with R on one N, and CH bearing X(O)n-R1 and N-R2)

| Cmpd. No. | R | R₁ | R₂ | X | n | $n_D^{30}$ or m.p. °C. or Constant |
|---|---|---|---|---|---|---|
| 109 | 3-Cl-phenyl | 2,4-dimethylpyrimidin-... (pyrimidine with CH₃) | —CH₃ | S | 0 | 125–128 |
| 110 | 3-Cl-phenyl | 2-isopropylphenyl | —CH₃ | S | 0 | 110–112 |
| 111 | 3-Cl-phenyl | 1-methyl-1,2,4-triazol-... | —CH₃ | S | 0 | thick oil |
| 112 | 3-Cl-phenyl | —C(=S)—O—CH₂CH₃ | —CH₃ | S | 0 | thick oil |
| 113 | 3-CF₃-phenyl | —CH₂CH₂C(=O)CH₃ | —CH₃ | S | 0 | thick oil |
| 114 | 2-F-4-nitrophenyl | 2-Cl-phenyl | —CH₃ | S | 0 | 55–57 |
| 115 | 4-Cl-phenyl | 2-Br-phenyl | —CH₃ | S | 0 | 120–122 |
| 116 | 2-F-phenyl | 2-F-phenyl | K—CH₃ | S | 0 | 110–113 |
| 117 | 2-F-phenyl | 4-OCH₃-phenyl | —CH₃ | S | 0 | 150–152 |

TABLE I-continued $$\underset{R_2}{\underset{|}{\underset{N}{\overset{R}{\underset{|}{N}}}}} \underset{O}{\overset{O}{\underset{\|}{C}}} - \underset{|}{\overset{|}{C}} - X(O)_n - R_1$$

| Cmpd. No. | R | R₁ | R₂ | X | n | $n_D^{30}$ or m.p. °C. or Constant |
|---|---|---|---|---|---|---|
| 118 | 2-Cl-C₆H₄ | 2-Cl-C₆H₄ | —CH₃ | S | 0 | thick oil |
| 119 | 2-F-C₆H₄ | 2-CH₃-C₆H₄ | —CH₃ | S | 0 | 122–123 |
| 120 | 2-F-C₆H₄ | 2-OCH₃-C₆H₄ | —CH₃ | S | 0 | thick oil |
| 121 | 2-F-C₆H₄ | 4-methyl-1,2,4-triazol-3-yl | —CH₃ | S | 0 | 140–144 |
| 122 | 2-F-C₆H₄ | 4-Br-C₆H₄ | —CH₃ | S | 0 | 67–71 |
| 123 | 2-F-C₆H₄ | 4-NO₂-C₆H₄ | —CH₃ | S | 0 | 160–164 |
| 124 | 2-F-C₆H₄ | C₆H₅ | —CH₃ | S | 0 | thick oil |
| 125 | 2-F-C₆H₄ | 3,4-Cl₂-C₆H₃ | —CH₃ | S | 0 | 120–122 |
| 126 | 2-F-5-CF₃-C₆H₃ | —CH₂COCH₃ | —CH₃ | S | 0 | thick oil |

TABLE I-continued
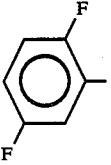
| Cmpd. No. | R | R₁ | R₂ | X | n | $n_D^{30}$ or m.p. °C. or Constant |
|---|---|---|---|---|---|---|
| 127 | 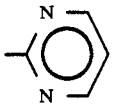 | 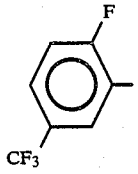 | —CH₃ | S | 0 | thick oil |
| 128 | 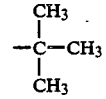 | 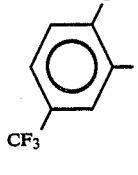 | —CH₃ | S | 0 | thick oil |
| 129 | 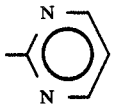 | 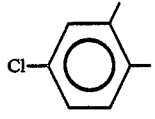 | —CH₃ | S | 0 | thick oil |
| 130 | 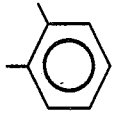 | 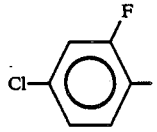 | —CH₃ | S | 0 | thick oil |
| 131 | 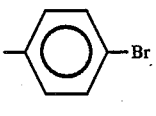 | 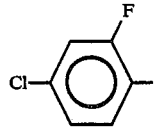 | —CH₃ | S | 0 | 128–131 |
| 132 | 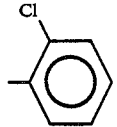 | 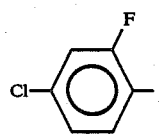 | —CH₃ | S | 0 | thick oil |
| 133 | 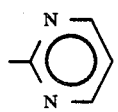 | 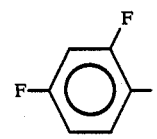 | —CH₃ | S | 0 | 157–160 |
| 134 | 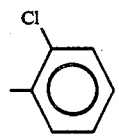 | 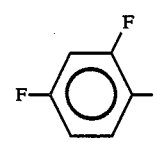 | —CH₃ | S | 0 | 95–97 |
| 135 | 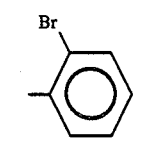 | Br | —CH₃ | S | 0 | thick oil |

TABLE I-continued $$\underset{R_2}{\overset{R}{\underset{|}{N}}}\overset{O}{\underset{\|}{C}}\underset{|}{\overset{|}{C}}\text{—}X(O)_n\text{—}R_1$$

| Cmpd. No. | R | $R_1$ | $R_2$ | X | n | $n_D^{30}$ or m.p. °C. or Constant |
|---|---|---|---|---|---|---|
| 136 | 2,4-difluorophenyl | 4-bromophenyl | —CH$_3$ | S | 0 | 69–71 |
| 137 | 2,4-difluorophenyl | pyrimidin-2-yl | —CH$_3$ | S | 0 | 78–81 |
| 138 | 2,4-difluorophenyl | —CH$_2$-(2-chlorophenyl) | —CH$_3$ | S | 0 | 95–98 |
| 139 | 3-fluoro-4-methylphenyl | 2-chlorophenyl | —CH$_3$ | S | 0 | thick oil |
| 140 | —CH$_3$ | 2-chlorophenyl | 2-fluorophenyl | S | 0 | 129–131 |
| 141 | 3-fluoro-4-methylphenyl | 2-chlorophenyl | —CH$_3$ | S | 0 | thick oil |
| 142 | —CH$_3$ | pyridin-2-yl | 2-fluorophenyl | S | 0 | 105–112 |
| 143 | —CH$_3$ | —CH$_2$COCH$_3$ | 2-fluorophenyl | S | 0 | thick oil |
| 144 | —CH$_3$ | 2-bromophenyl | 2-fluorophenyl | S | 0 | 105–110 |
| 145 | 3-fluoro-4-methylphenyl | pyrimidin-2-yl | —CH$_3$ | S | 0 | 157–160 |

TABLE I-continued

Structure:

$$\begin{array}{c} R-N \\ \phantom{R-}| \\ O=C \\ \phantom{O=}\diagdown N-R_2 \end{array} \begin{array}{c} O \\ \| \\ C-CH-X(O)_n-R_1 \\ \phantom{C-}| \end{array}$$

| Cmpd. No. | R | $R_1$ | $R_2$ | X | n | $n_D^{30}$ or m.p. °C. or Constant |
|---|---|---|---|---|---|---|
| 146 | 3-fluoro-4-methylphenyl 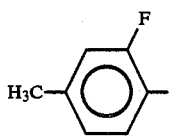 | pyrimidin-2-yl 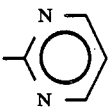 | —CH$_3$ | S | 0 | 180–185 |
| 147 | —CH$_3$ | pyrimidin-2-yl 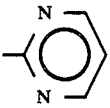 | 2,5-difluorophenyl 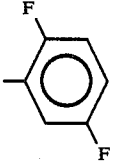 | S | 0 | 200–207 |
| 148 | —CH$_3$ | 2-methylphenyl 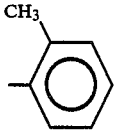 | 2,5-difluorophenyl 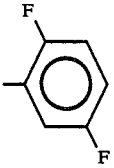 | S | 0 | 115–120 |
| 149 | —CH$_3$ | phenyl 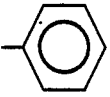 | 2-fluorophenyl 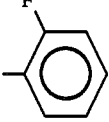 | S | 0 | 134–136 |
| 150 | 2-fluoro-5-trifluoromethylphenyl 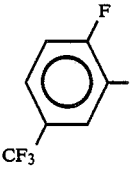 | 2-chlorophenyl 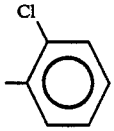 | —CH$_3$ | S | 0 | thick oil |
| 151 | —CH$_3$ | phenyl 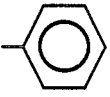 | 2,5-difluorophenyl 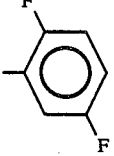 | S | 0 | 160–170 |
| 152 | —CH$_3$ | —CH$_2$CH$_2$COCH$_3$ | 2,5-difluorophenyl 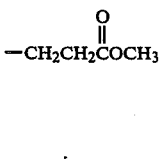 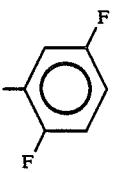 | S | 0 | 45–50 |
| 153 | —CH$_3$ | 1,4,5,6-tetrahydropyrimidin-2-yl 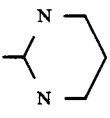 | 2-fluoro-4-methylphenyl 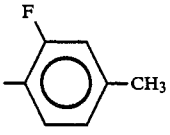 | S | 0 | 160–165 |

TABLE I-continued $$\underset{O=\underset{|}{\overset{|}{\underset{R_2}{N}}}}{\overset{R\diagdown N\diagup\overset{O}{\overset{\|}{C}}\diagdown \overset{|}{C}\diagup X(O)_n-R_1}{}}$$

| Cmpd. No. | R | $R_1$ | $R_2$ | X | n | $n_D^{30}$ or m.p. °C. or Constant |
|---|---|---|---|---|---|---|
| 154 | —CH$_3$ | 4-Cl-phenyl | 4-Br-2-F-phenyl | S | 0 | 120–124 |
| 155 | 2-F-phenyl | phenyl | —CH$_3$ | O | 0 | 128–131 |
| 156 | 2,4-diF-phenyl | phenyl | —CH$_3$ | O | 0 | 162–165 |
| 157 | 2-F-4-CH$_3$-phenyl | phenyl | —CH$_3$ | O | 0 | 112–117 |

The compounds listed in the foregoing Table I were tested for herbicidal activity by various methods and at various rates of application. Some were tested by more than one method or at more than one rate, but at least one method is shown for each compound to exhibit utility. The following examples are for illustrative purposes only and are not intended as necessarily representative of the overall testing performed. As one skilled in the art is aware, in herbicidal testing a significant number of factors that are not readily controllable can affect the results of individual tests. For example, the results may vary depending on environmental factors, such as amount of sunlight and water, soil type, pH of the soil, temperature, and humidity, among other factors. Also, the depth of planting and the application rate of the herbicide, as well as the nature of crops being tested, can affect the results of the test. Results may vary from crop to crop and within the crop varieties. The methods and activity are as follows:

PRE-EMERGENCE HERBICIDAL EVALUATION

Flats were filled with sandy loam soil containing a fungicide and fertilizer. The soil was leveled and rows of grassy weeds, broadleaf weeds and yellow nutsedge (*Cyperus esculentus*), were planted thickly enough so that several seedlings emerged per inch of row. The grassy weeds were: foxtail (Setaria spp.), watergrass (*Echinochloa crusgalli*), wild oat (*Avena fatua*) and prickly sida (*Sida spinosa*). Broadleaf weeds utilized were annual morningglory (*Ipomoea purpurea*), velvetleaf (*Abutilon theophrasti*), mustard (*Brassica juncea*), and curly dock (*Rumex crispus*).

One day after planting, the flats were sprayed with a solution of a test compound at a rate of 80 gallons of solution per acre with the compound being applied at a rate of 4 pounds per acre (4.48 kg/ha).

The solutions of the test compounds were made by weighing out 333 mg of the test compound into a 60 ml wide-mouth bottle, dissolving it in 25 ml of acetone containing 1% Tween ® 20 (polyoxyethylene sorbitan monolaurate emulsifier). Additional solvents, not exceeding 5 ml, were used if needed to dissolve the compound. A 20.5 ml aliquot was taken from the stock solution and diluted with 25 ml of an acetone:water mixture (19:1) containing 1% Tween ® 20. This was used as the spray solution.

The flats were returned to the greenhouse after spraying and watered daily by sprinkling. The degree of weed control was estimated and recorded 3 weeks after treatment, as percentage control compared to the growth of the same species in an untreated check flat of the same age.

The percent control is based on the total injury to the plants due to all factors, including inhibited germination, killing of the plant tissue after emergence, stunting, malformation, chlorosis, and other types of injury. The control ratings vary from 0 to 100 percent, where 0 represents no effect with growth equal to the untreated control, and 100 represents complete kill; (—) indicates the compound was not tested.

POST-EMERGENCE HERBICIDAL EVALUATION

The soil was prepared and seeded with the same varieties as described for the pre-emergence test. The flats were placed in the greenhouse at 70°–85° F. and watered by sprinkling. Twelve to fourteen days after planting, the flats were sprayed at a rate of 80 gallons of solution per acre. The compound was applied at the rate of 4 pounds/acre (4.48 kg/ha). The spray solution was made up similarly to that described for the pre-emergence evaluation.

The flats were returned to the greenhouse after spraying and watered daily without wetting the foliage. Three weeks after treatment the degree of weed control was estimated and recorded as percentage control compared to the growth of the same species in an untreated check flat of the same age. The percent control ratings were assigned on the same basis as for the pre-emergence evaluation.

The following Table II contains the results of these tests, in terms of average control of the three grasses, four broadleaf weeds, and yellow nutsedge, respectively, in both pre- and post-emergence evaluations.

TABLE II

| Compound Nbr. | Pre-Emergence Control | | | Post-Emergence Control | | |
|---|---|---|---|---|---|---|
| | YNS | AVG | AVB | YNS | AVG | AVB |
| 1 | 0 | 82 | 73 | 0 | 47 | 100 |
| 2 | 0 | 80 | 65 | 0 | 23 | 100 |
| 3 | 0 | 38 | 88 | 0 | 42 | 93 |
| 4 | N | 35 | 79 | 0 | 0 | 0 |
| 5 | 0 | 73 | 91 | — | 43 | 99 |
| 6 | 0 | 77 | 94 | — | 73 | 99 |
| 7 | 0 | 73 | 98 | 0 | 27 | 45 |
| 8 | 0 | 73 | 98 | 0 | 40 | 91 |
| 9 | 0 | 78 | 99 | 0 | 57 | 93 |
| 10 | 0 | 77 | 95 | 0 | 72 | 100 |
| 11 | 0 | 48 | 93 | 0 | 0 | 33 |
| 12 | 35 | 78 | 68 | 20 | 97 | 98 |
| 13 | 0 | 78 | 66 | 0 | 67 | 95 |
| 14 | 0 | 73 | 100 | 0 | 72 | 98 |
| 15 | 100 | 65 | 69 | 0 | 98 | 100 |
| 16 | 0 | 55 | 98 | 0 | 100 | 89 |
| 17 | 0 | 38 | 69 | 0 | 0 | 69 |
| 18 | 20 | 72 | 81 | 0 | 100 | 100 |
| 19 | 0 | 17 | 71 | 0 | 0 | 55 |
| 20 | 0 | 68 | 91 | 10 | 100 | 100 |
| 21 | 0 | 83 | 85 | 40 | 98 | 98 |
| 22 | 0 | 80 | 88 | 35 | 97 | 100 |
| 23 | 0 | 83 | 91 | 25 | 95 | 99 |
| 24 | 0 | 72 | 80 | 0 | 82 | 60 |
| 25 | 0 | 52 | 83 | 0 | 78 | 84 |
| 26 | 0 | 67 | 88 | 10 | 100 | 100 |
| 27 | 0 | 63 | 90 | 0 | 88 | 99 |
| 28 | 0 | 75 | 75 | 0 | 100 | 100 |
| 29 | 0 | 30 | 66 | 0 | 53 | 74 |
| 30 | 25 | 58 | 40 | 20 | 67 | 98 |
| 31 | 0 | 50 | 85 | 0 | 52 | 73 |
| 32 | 0 | 53 | 63 | 0 | 57 | 88 |
| 33 | 0 | 55 | 88 | 0 | 93 | 98 |
| 34 | 0 | 68 | 84 | 0 | 97 | 100 |
| 35 | 0 | 70 | 98 | 10 | 92 | 100 |
| 36 | 0 | 73 | 83 | 20 | 92 | 100 |
| 37 | 0 | 20 | 34 | 0 | 48 | 91 |
| 38 | 0 | 25 | 21 | 0 | 7 | 38 |
| 39 | 0 | 22 | 21 | 0 | 0 | 31 |
| 40 | 0 | 87 | 70 | 20 | 97 | 100 |
| 41 | 0 | 78 | 73 | 0 | 92 | 10 |
| 42 | 0 | 78 | 91 | 10 | 93 | 100 |
| 43 | 0 | 67 | 96 | 20 | 93 | 100 |
| 44 | 0 | 65 | 94 | 0 | 97 | 100 |
| 45 | 0 | 12 | 43 | 0 | 83 | 99 |
| 46 | 0 | 53 | 64 | — | 77 | 100 |
| 47 | 0 | 57 | 71 | — | 48 | 95 |
| 48 | 0 | 50 | 23 | — | 90 | 100 |
| 49 | 0 | 22 | 10 | — | 35 | 60 |
| 50 | 0 | 60 | 75 | — | 92 | 100 |
| 51 | 0 | 58 | 88 | 0 | 62 | 100 |
| 52 | 0 | 62 | 94 | 0 | 73 | 100 |
| 53 | 0 | 63 | 96 | 10 | 97 | 100 |
| 54 | 0 | 53 | 90 | 0 | 70 | 100 |
| 55 | 0 | 40 | 58 | 0 | 18 | 41 |
| 56 | 0 | 53 | 80 | 15 | 75 | 95 |
| 57 | 0 | 33 | 49 | 15 | 65 | 98 |
| 58 | 0 | 37 | 55 | 0 | 58 | 98 |
| 59 | 0 | 42 | 38 | 30 | 95 | 99 |
| 60 | 0 | 38 | 39 | 0 | 55 | 99 |
| 61 | 0 | 28 | 39 | 10 | 85 | 100 |
| 62 | 0 | 20 | 45 | 0 | 35 | 48 |
| 63 | 0 | 27 | 26 | 0 | 92 | 100 |
| 64 | 0 | 23 | 44 | — | 45 | 81 |
| 65 | — | 18 | 0 | 0 | 32 | 64 |
| 66 | — | 23 | 54 | 0 | 95 | 99 |
| 67 | 0 | 0 | 0 | 0 | 23 | 21 |
| 68 | 0 | 10 | 31 | 10 | 7 | 21 |
| 69 | 0 | 0 | 0 | 0 | 20 | 86 |
| 70 | 0 | 38 | 75 | 35 | 33 | 99 |
| 71 | 0 | 40 | 56 | 0 | 18 | 84 |
| 72 | 0 | 48 | 65 | 0 | 65 | 99 |
| 73 | 0 | 57 | 56 | 0 | 73 | 100 |
| 74 | 0 | 63 | 81 | 0 | 82 | 100 |
| 75 | 0 | 0 | 9 | 0 | 25 | 94 |
| 76 | 0 | 67 | 91 | 0 | 85 | 98 |
| 77 | 0 | 63 | 85 | 0 | 97 | 100 |
| 78 | 0 | 65 | 93 | 0 | 92 | 100 |
| 79 | 0 | 63 | 96 | 0 | 92 | 100 |
| 80 | 0 | 40 | 38 | 0 | 0 | 81 |
| 81 | 0 | 73 | 84 | 35 | 97 | 98 |
| 82 | 0 | 72 | 84 | 10 | 97 | 99 |
| 83 | 0 | 73 | 88 | 15 | 98 | 99 |
| 84 | 0 | 75 | 100 | 0 | 47 | 93 |
| 85 | 0 | 67 | 95 | 0 | 77 | 97 |
| 86 | 0 | 67 | 100 | 0 | 67 | 97 |
| 87 | 0 | 67 | 93 | 0 | 60 | 85 |
| 88 | 0 | 57 | 80 | 0 | 47 | 92 |
| 90 | 0 | 17 | 55 | 0 | 0 | 48 |
| 91 | 0 | 13 | 38 | 0 | 3 | 30 |
| 92 | 0 | 97 | 100 | 0 | 30 | 98 |
| 93 | 25 | 78 | 100 | 40 | 93 | 100 |
| 95 | 0 | 78 | 100 | 0 | 20 | 95 |
| 96 | 0 | 77 | 98 | 35 | 77 | 100 |
| 98 | 0 | 10 | 90 | 0 | 100 | 100 |
| 99 | 0 | 48 | 100 | 0 | 93 | 100 |
| 100 | 0 | 93 | 100 | 0 | 62 | 97 |
| 101 | 0 | 73 | 100 | 0 | 87 | 100 |
| 102 | 0 | 77 | 100 | 0 | 20 | 100 |
| 103 | 0 | 67 | 100 | 0 | 37 | 98 |
| 104 | 0 | 20 | 78 | 0 | 0 | 35 |
| 105 | 70 | 58 | 100 | 0 | 12 | 73 |
| 106 | 57 | 83 | 70 | 0 | 0 | 40 |
| 107 | 50 | 55 | 100 | 0 | 3 | 67 |
| 108 | 0 | 86 | 99 | 0 | 77 | 100 |
| 109 | 0 | 92 | 80 | 0 | 40 | 100 |
| 110 | — | — | — | 0 | 0 | 63 |
| 111 | 0 | 84 | 93 | 0 | 60 | 100 |
| 112 | 0 | 58 | 100 | 0 | 17 | 100 |
| 113 | 0 | 95 | 100 | 0 | 77 | 100 |
| 114 | 0 | 0 | 45 | 0 | 0 | 45 |
| 115 | 0 | 62 | 73 | 0 | 33 | 73 |
| 116 | 0 | 98 | 100 | 20 | 93 | 97 |
| 117 | 0 | 98 | 98 | 0 | 57 | 77 |
| 118 | 0 | 78 | 88 | 0 | 27 | 37 |
| 119 | 0 | 98 | 100 | 0 | 93 | 100 |
| 120 | 0 | 98 | 100 | 0 | 99 | 100 |
| 121 | 0 | 98 | 93 | 0 | 67 | 97 |
| 122 | 0 | 100 | 98 | 0 | 97 | 97 |
| 123 | 0 | 98 | 99 | 0 | 94 | 100 |
| 124 | 0 | 98 | 99 | 0 | 100 | 100 |
| 125 | 0 | 98 | 100 | 0 | 100 | 100 |
| 126 | 0 | 92 | 98 | 0 | 85 | 96 |
| 127 | 0 | 97 | 100 | 0 | 100 | 100 |
| 128 | 0 | 77 | 73 | 0 | 90 | 97 |
| 129 | 0 | 88 | 97 | 0 | 87 | 100 |

TABLE II-continued

| Compound Nbr. | Pre-Emergence Control | | | Post-Emergence Control | | |
|---|---|---|---|---|---|---|
| | YNS | AVG | AVB | YNS | AVG | AVB |
| 130 | 0 | 83 | 97 | — | 100 | 100 |
| 131 | 0 | 70 | 95 | 0 | 97 | 98 |
| 132 | 0 | 78 | 100 | 0 | 98 | 100 |
| 133 | 0 | 67 | 97 | 0 | 100 | 99 |
| 134 | 0 | 73 | 100 | 0 | 98 | 100 |
| 135 | 0 | 95 | 97 | 0 | 97 | 97 |
| 136 | 0 | 95 | 100 | 0 | 47 | 90 |
| 137 | 0 | 95 | 100 | 0 | 100 | 100 |
| 138 | 0 | 95 | 97 | 0 | 87 | 100 |
| 139 | 0 | 83 | 100 | 0 | 58 | 100 |
| 140 | 0 | 93 | 100 | 0 | 100 | 100 |
| 142 | 0 | 100 | 100 | 0 | 100 | 100 |
| 143 | 0 | 87 | 97 | 0 | 100 | 97 |
| 144 | 0 | 93 | 100 | 0 | 37 | 100 |
| 145 | 0 | 37 | 100 | 0 | 0 | 100 |
| 148 | 0 | 98 | 100 | 0 | 100 | 100 |
| 149 | 0 | 92 | 100 | 0 | 100 | 100 |
| 151 | 0 | 27 | 100 | 0 | 30 | 97 |
| 152 | 0 | 97 | 100 | 0 | 100 | 100 |
| 153 | 0 | 47 | 83 | 0 | 0 | 3 |
| 154 | 0 | 37 | 92 | 0 | 0 | 17 |
| 155 | 0 | 3 | 77 | 0 | 0 | 23 |
| 156 | 0 | 0 | 30 | 0 | 0 | 0 |
| 157 | 0 | 0 | 27 | 0 | 0 | 28 |

Rating at 4 lb/A
YNS — Yellow nutsedge
AVG — grasses
AVB — broadleaf weeds

Compounds 155, 156 and 157 showed good control of velvetleaf (*Abutilon theophrasti*) in the pre-emergence herbicidal evaluation at 4 lb/A application rate as shown in the following Table III.

TABLE III

| Cmpd. No. | ABUTH |
|---|---|
| 155 | 90 |
| 156 | 90 |
| 157 | 9 |

Six compounds not depicted in the foregoing Table II were tested according to the following pre- and post-emergence controlled light evaluation.

CONTROLLED LIGHT - PRE-EMERGENCE MULTI-WEED/MULTI-CROP EVALUATION

Flats were filled with sandy loam soil containing a fungicide. The soil was leveled and rows of 4 grassy weeds, 5 broadleaf weeds and three crops were planted thickly enough so that several seedlings emerged per inch of row. Grassy weeds utilized were blackgrass (*Alopecurus myosuroides*), perennial ryegrass (*Lolium perenne*), wild oats (*Avena fatua*) and poverty brome (*Bromus sterilis*). Broadleaf weeds utilized were scented mayweed (*Matricaria recutita*), common chickweed (*Stellaria media*), bedstraw (*Galium aparine*), carrot (*Daucus carota*) and wild mustard (*Brassica kaber*). Crops utilized were sugarbeet (*Beta vulgaris*), barley (*Hordeum vulgare*) and wheat (*Triticum aestivum*).

After seeding, the flats were immediately sprayed with solutions of the selected test compounds at a rate of 40 gallons of solution per acre with the compound being applied at a rate of 2 pounds per acre (2.24 kg/ha).

The solutions of the test compounds were made by weighing 240 mg of the test compound into a 60 ml wide-mouth bottle, dissolving it in 20 ml of acetone containing 0.5% polyoxyethylene sorbitan monolaurate emulsifier and then brought to volume with 20 ml of water.

The flats were placed in a greenhouse with whitewash maintained on the glazing to reduce light intensity to approximately one-half sun-light and in which the temperature was maintained between 15°–24° C.

The degree of control was estimated and recorded from 3–4 weeks after treatment as percentage compared to the growth of the same species in an untreated flat of the same age. Percent control was based on the total injury to the plants due to all factors including inhibited germination, killing of the plant tissue after emergence, stunting, malformation, chlorosis and other types of injury. The control ratings ranged from 0–100 percent, with 0 representing no effect with growth equal to the untreated control, and 100 representing complete kill. The following Table IV contains the results of these tests in terms of average control of the four grasses, five broadleaf weeds and three crops in these evaluations.

TABLE IV

| | | Pre-Emergence | | | | |
|---|---|---|---|---|---|---|
| Cmpd. No. | Rate (lb/A) | Average Grasses | Average Broadleaf | Sugarbeet | Barley | Wheat |
| 89 | 0.25 | 24 | 36 | 65 | 0 | 0 |
| | 0.50 | 38 | 43 | 100 | 20 | 15 |
| | 1.00 | 54 | 62 | 100 | 30 | 20 |
| | 2.00 | 68 | 81 | 100 | 60 | 50 |
| 94 | 0.25 | 83 | 60 | 100 | 70 | 50 |
| | 0.50 | 86 | 60 | 100 | 75 | 60 |
| | 1.00 | 93 | 90 | 100 | 90 | 70 |
| | 2.00 | 96 | 91 | 100 | 95 | 90 |
| 97 | 1.00 | 0 | 15 | 50 | 0 | 0 |
| 141 | 0.25 | 16 | 36 | 15 | 0 | 0 |
| | 0.50 | 39 | 57 | 0 | 0 | 0 |
| | 1.00 | 80 | 60 | 20 | 20 | 25 |
| | 2.00 | 94 | 84 | 70 | 30 | 30 |
| 146 | 1.00 | 21 | 45 | 10 | 15 | 0 |
| 147 | 1.00 | 65 | 75 | 100 | 30 | 40 |

CONTROLLED LIGHT POST-EMERGENCE MULTI-WEED/MULTI-CROP EVALUATION

The soil was prepared and seeded as described for the pre-emergence test. Flats containing seeds of broadleaf species were placed in the greenhouse 21 days, and flats containing seeds of grass species were placed in the greenhouse 14 days before spraying at the same rates as in the pre-emergence evaluation.

After spraying, the flats were returned to the greenhouse and watered daily. Three to four weeks after treatment, the degree of control was estimated and the percent control ratings were assigned on the same basis as for the pre-emergence evaluation.

The following Table V contains the results of these tests in terms of average control of the four grasses, five broadleaf weeds and three crops in these evaluations.

TABLE V

| | | Post-Emergence | | | | |
|---|---|---|---|---|---|---|
| Cmpd. No. | Rate (lb/A) | Average Grasses | Average Broadleaf | Sugarbeet | Barley | Wheat |
| 89 | 0.25 | 24 | 68 | 100 | 15 | 20 |
| | 0.50 | 41 | 75 | 100 | 20 | 25 |
| | 1.00 | 75 | 92 | 100 | 60 | 50 |
| | 2.00 | 95 | 98 | 100 | 90 | 80 |
| 94 | 0.25 | 72 | 74 | 100 | 60 | 74 |
| | 0.50 | 75 | 83 | 100 | 95 | 85 |
| | 1.00 | 84 | 88 | 100 | 100 | 88 |
| | 2.00 | 100 | 97 | 100 | 100 | 93 |
| 97 | 1.00 | 0 | 50 | 100 | 0 | 0 |
| 141 | 0.25 | 4 | 53 | 50 | 0 | 0 |
| | 0.50 | 25 | 65 | 60 | 0 | 0 |
| | 1.00 | 40 | 69 | 75 | 0 | 0 |
| | 2.00 | 65 | 81 | 80 | 35 | 20 |

TABLE V-continued

| Cmpd. No. | Rate (lb/A) | Post-Emergence | | | | |
|---|---|---|---|---|---|---|
| | | Average Grasses | Average Broadleaf | Sugar-beet | Barley | Wheat |
| 146 | 1.00 | 43 | 60 | 95 | 0 | 0 |
| 147 | 1.00 | 93 | 80 | 100 | 40 | 45 |

PRE-EMERGENCE

MULTI-WEED/MULTI-CROP EVALUATION

Compound 150 was evaluated at applications rates of 0.5 and 2.0 lb active ingredient/acre (0.56 and 2.24 kg/ha, respectively) for pre-emergence activity against a number of weed and crop species. The procedure was generally similar to the pre-emergence evaluation described above. Broadleaf weed species utilized were annula morningglory, nightshade, velvetleaf, mustard, pigweed (*Amaranthus retroflexus*), cocklebur (*Xanthioum pennsylvanicum*), and jimsonweed (*Datura stramonium*). Grassy weeds utilized were: foxtail, watergrass, wild oat, downy brome (*Bromus tectorum*), annual ryegrass (*Lolium multiflorum*) and shattercane (*Sorghum bicolor*). Yellow nutsedge was also included in these tests. Crops included were: soybean (*Glycine max*), rice (*Oryza sativa*), cotton (*Gossypium herbaceum*), corn (*Zea mays*), wheat (*Triticum aestivum*), milo (*Sorghum vulgare*) and sugarbeets (*Beta vulgaris*).

The following Table VI contains the results of these tests, in terms of average control of the seven broadleaf weeds, six grassy weeds, and nutsedge, and injury to the crop species, with visual ratings ranging from 0% (no injury) to 100% (complete kill) as compared to untreated control flats.

TABLE VI

| Cmpd. No. | Rate lb/A | Pre-Emergence | | | | | | | | | |
|---|---|---|---|---|---|---|---|---|---|---|---|
| | | Broad leaf-weeds | Grasses | Nut-sedge | Soy-bean | Corn | Rice | Cotton | Wheat | Milo | Sugar-beets |
| 150 | 0.50 | 17 | 11 | 0 | 10 | 20 | 0 | 35 | 15 | 0 | 100 |
| | 1.00 | 38 | 53 | 0 | 25 | 25 | 20 | 25 | 25 | 0 | 100 |

POST-EMERGENCE MULTI-WEED/MULTI-CROP EVALUATION

Compound 150 was evaluated at applications rates of 0.10, 0.50 and 2.00 lb active ingredient/acre (0.112, 0.56 and 2.24 kg/ha, respectively) for preemergence activity against a number of weed and crop species. The procedure was generally similar to the pre-emergence evaluation described above. Broadleaf weed species utilized were annual morningglory, nightshade, velvetleaf, mustard, pigweed (*Amaranthus retroflexus*), cocklebur (*Xanthioum pennsylvanicum*), and jimsonweed (*Datura stramonium*). Grassy weeds utilized were: foxtail, watergrass, wild oat, downy brome (*Bromus tectorum*), annual ryegrass (*Lolium multiflorum*) and shattercane (*Sorghum bicolor*). Yellow nutsedge was also included in these tests. Crops included were: soybean (*Glycine max*), rice (*Oryza sativa*), cotton (*Gossypium herbaceum*), corn (*Zea mays*), winter wheat (*Triticum aestivum*), milo (*Sorghum vulgare*) and sugarbeets (*Beta vulgaris*).

The following Table VII contains the results of these tests, in terms of average control of the seven broadleaf weeds, six grassy weeds, and nutsedge, and injury to the crop species, with visual ratings ranging from 0% (no injury) to 100% (complete kill) as compared to untreated control flats.

TABLE VII

| Cmpd. No. | Rate lb/A | Post-Emergence | | | | | | | | | |
|---|---|---|---|---|---|---|---|---|---|---|---|
| | | Broad leaf-weeds | Grasses | Nut-sedge | Soy-bean | Corn | Rice | Cotton | Wheat | Milo | Sugar-beet |
| 150 | 0.50 | 21 | 6 | 0 | 30 | 20 | 20 | 0 | 0 | 0 | 90 |
| | 1.00 | 81 | 54 | 0 | 80 | 30 | 30 | 10 | 35 | 15 | 100 |

FORMULATIONS

In practice, a pure compound can be used as a herbicide. However, in general, the compounds are first formulated with one or more inert carriers or diluents suitable for herbicidal use, before being applied.

The compositions or formulations, including a compound as described herein, may exist in any one of a number of solid or liquid forms. Examples of solid forms are dusts, granules, microcapsules, tablets, powders and the like. Examples of liquid forms are emulsifiable concentrates, flowables, liquid concentrates and pastes. Such compositions may contain, in addition to the active compound or compounds, various carriers or diluents; surface active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcium carbonate, silica, clay, etc.; ground synthetic minerals such as various silicates and alumino-silicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Microcapsules consist of fully enclosed droplets or granules containing the active materials in which the enclosing material is an inert porous membrane, arranged to allow escape of the enclosed materials to the surrounding medium at controlled rates over a specified period of time. Encapsulated droplets are typically about 1 to 50 microns in diameter. The enclosed liquid typically constitutes about 50 to 95% of the weight of the entire capsule, and may contain an amount of solvent in addition to the active materials. Encapsulated granules are characterized by porous membranes sealing the openings of the granule carrier pores, trapping the liquid containing the active components inside for controlled release. A typical granule size ranges from 1 millimeter to 1 centimeter in diameter. In agricultural usage, the granule size is generally about 1 to 2 millimeters in diameter. Granules formed by extrusion, agglomeration or prilling are useful in the present invention, as well as the materials in their naturally occurring form. Examples of such carriers are vermiculite, sintered clay granules, kaolin, attapulgite clay, sawdust and granular carbon. Useful encapsulating materials include natural and synthetic rubbers, cellulosic materials, styrene-butadiene copolymers, polyacrylonitriles, polyacrylates, polyesters, polyamides, polyureas, polyurethanes and starch xanthates.

Wettable powders, flowables, and pastes are obtained by mixing and milling an active compound with one or more dispersing/wetting agents and/or carriers or diluents. Common dispersing/wetting agents are, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes or higher boiling aromatic hydrocarbons. To obtain stable suspensions or emulsions in application water, wetting agents are generally also added.

It is possible to use highly concentrated liquid compositions containing up to about 95% by weight of the active compound, or even the active compound alone for those compounds which are liquids, when applying the compound in the form of a finely divided liquid by use of various atomizing equipment, for example by airplane crop spraying techniques. For other purposes, however, the various types of compositions which can be utilized for these compounds will contain varying amounts of the compound according to the type of composition and the intended use.

In general, compositions may contain from 0.1 to 95% of the active compound, more preferably from 0.5 to 90%. Some typical compositions will contain an active compound as follows: wettable powders, flowables and pastes—20 to 90% active compound; oil suspensions, emulsions, solutions and emulsifiable concentrates—1 to 90% active compound; aqueous suspensions—10 to 50% active compound; dusts and powders—1 to 25% active compound; granules and pellets—0.5 to 20% active compound.

The rate of application of the active compound to a locus to be controlled will depend on the nature of the seeds and plants to be controlled and will vary from about 0.05 to about 50 pounds per acre (about 0.06 to about 56 kg/ha).

In addition to the active compound and the various agents utilized in preparing compositions and formulations mentioned above, such compositions may also contain one or more other active compounds of the type mentioned herein as well as other pesticidal agents, such as herbicides, fungicides, insecticides, acaricides, nematocides, bactericides, and plant growth regulators. Such compositions may also contain soil disinfectants or fumigants and may further contain fertilizers, thus making it possible to provide multi-purpose compositions containing one or of the compounds described herein as well as, optionally, other pesticides and also fertilizers, all intended and formulated for use at the same locus.

Compositions containing one or more of the active compounds described, in a herbicidally effective amount, may be applied to the plant or locus to be controlled in any conventional manner. Thus, powders and various liquid compositions containing the active compound can be applied by the use of power dusters, boom and hand sprayers and spray dusters, or applied from airplanes as mists or sprays. When applied in the latter method they may be effective in very low dosages. To modify or control growth of germinating seeds or emerging seedlings liquid compositions may be applied to the soil with conventional methods and may be distributed in the soil to a depth of one-half inch below the soil surface. The compositions need not be admixed with the soil particles but can be applied merely by sprinkling on the surface of the soil.

Compositions including active compounds may also be applied by addition to irrigation waters supplied to the field to be treated. This method of application permits penetration of the compounds into the soil as the water is absorbed therein.

| EXAMPLES OF TYPICAL COMPOSITIONS | | | |
|---|---|---|---|
| Ingredient | Weight % | | |
| Oil | | | |
| Compound 1 | 1 | | |
| Oil solvent-heavy aromatic naphtha | 99 | | |
| Total | 100 | | |
| Emulsifiable Concentrate | | | |
| Compound 2 | 50 | | |
| Kerosene | 45 | | |
| Emulsifying agent (mixture of long chain ethoxylated polyethers with long chain sulfonate) | 5 | | |
| Total | 100 | | |
| Emulsifiable Concentrate | | | |
| Compound 3 | 90 | | |
| Kerosene | 5 | | |
| Emulsifying agent (mixture of long chain ethoxylated polyethers with long chain sulfonate) | 5 | | |
| Total | 100 | | |
| Dusts and/or Powders | | | |
| Ingredient | Wt. % | Wt. % | Wt. % |
| Compound 4 | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| Total | 100.0 | 100.0 | 100.0 |

What is claimed is:

1. A compound having the formula

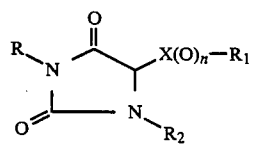

wherein
R is $C_1$–$C_3$ alkyl, phenyl or phenyl substituted with one or more alkyl, alkoxy, halo, haloalkyl or nitro;
$R_1$ is phenyl or phenyl substituted with one or more alkyl, alkoxy, halo, haloalkyl or nitro;

$R_2$ is lower alkyl, phenyl or phenyl substituted with one or more alkyl, halo or haloalkyl;

X is sulfur or oxygen; and n is an integer from 0 to 2.

2. A compound according to claim 1 wherein R is phenyl or phenyl substituted with one or more alkyl, alkoxy, halo, haloalkyl, nitro or combinations thereof.

3. A compound according to claim 1 wherein $R_2$ is $C_1$-$C_3$ alkyl.

4. A compound according to claim 1 wherein X is sulfur.

5. A compound according to claim 4 wherein n is the integer 0.

6. A compound according to claim 4 wherein n is 2.

7. A compound according to claim 1 wherein X is oxygen and n is the integer 0.

8. A compound according to claim 1 wherein R is $C_1$-$C_3$ alkyl.

9. A compound according to claim 3 wherein R is phenyl or phenyl substituted with one or more alkyl, alkoxy, halo, haloalkyl or nitro; $R_2$ is methyl; X is sulfur; and n is 0.

10. A compound according to claim 9 selected from the group consisting of:
3-(2-fluorophenyl)-5-(phenylthio)-1-methylimidazolidine-2,4-dione,
3-(2-fluorophenyl)-5-(2-fluorophenylthio)-1-methylimidazolidine-2,4-dione,
3-(2-fluorophenyl)-5-(2-chlorophenylthio)-1-methylimidazole-2,4-dione,
3-(2-fluorophenyl)-5-(2-bromophenylthio)-1-methylimidazolidine-2,4-dione,
3-(2-fluorophenyl)-5-(2-isopropylphenylthio)-1-methylimidazolidine-2,4-dione,
3-(2-fluorophenyl)-5-(4-chlorophenylthio)-1-methylimidazolidine-2,4-dione,
3-(2-fluorophenyl)-5-(4-nitrophenylthio)-1-methylimidazolidine-2,4-dione,
5-(2-nitrothiophenoxy)-3-(2-fluorophenyl)-1-methylimidazolidine-2,4-dione,
3-(2-fluorophenyl)-5-(2-methylphenylthio)-1-methylimidazolidine-2,4-dione,
3-(2-fluorophenyl)-5-(4-bromophenylthio)-1-methylimidazolidine-2,4-dione,
3-(2-fluorophenyl)-5-(2-methoxyphenylthio)-1-methylimidazolidine-2,4-dione,
3-(2,5-difluorophenyl)-5-(2-chlorophenylthio)-1-methylimidazolidine-2,4-dione,
3-(2,5-difluorophenyl)-5-(2-bromophenylthio)-1-methylimidazolidine-2,4-dione,
3-(2,5-difluorophenyl)-5-(4-chlorophenylthio)-1-methylimidazolidine-2,4-dione and
3-(2,5-difluorophenyl)-5-(2-bromophenylthio)-1-methylimidazolidine-2,4-dione.

11. A compound according to claim 2 wherein $R_1$ is phenyl or phenyl substituted with alkyl, alkoxy, halo, haloalkyl, nitro or combinations thereof; $R_2$ is $C_1$-$C_3$ lower alkyl; X is sulfur; and n is an integer from 0-2.

12. A compound according to claim 11 wherein n is the integer 2.

13. The compound 5-(4-fluorophenylsulfonyl)-3-(3-chlorophenyl)-1-methylimidazolidine-2,4-dione according to claim 12.

14. A compound according to claim 11 wherein $R_2$ is methyl.

15. A compound according to claim 8 wherein R is $C_1$-$C_3$ lower alkyl; $R_1$ is phenyl or phenyl substituted with alkyl, alkoxy, or halo; $R_2$ is phenyl, phenyl substituted with one or moe alkyl, halo or haloalkyl; X is sulfur; and n is the integer 0.

16. A compound according to claim 15 wherein R is methyl.

17. A compound according to claim 8 wherein $R_1$ is phenyl or phenyl substituted with one or more alkyl, alkoxy or halo; and $R_2$ is phenyl or phenyl substituted with one or more alkyl, halo or haloalkyl.

18. A compound according to claim 15 selected from the group consisting of:
1-(2-fluorophenyl)-5-(2-chlorophenyl)thio-3-methylimidazolidine-2,4-dione,
1-(2-fluorophenyl)-5-(2-bromophenyl)thio-3-methylimidazolidine-2,4-dione,
1-(2,5-difluorophenyl)-5-(2-chlorophenyl)thio-3-methylimidazolidine-2,4-dione and
1-(2-fluorophenyl)-5-phenylthio-3-methylimidazolidine-2,4-dione.

19. A compound according to claim 7 wherein R is phenyl substituted with one or more halo or alkyl; $R_1$ is phenyl or phenyl substituted with one or more halo or alkyl; $R_2$ is $C_1$-$C_3$ lower alkyl; X is oxygen and n is the integer 0.

20. A compound according to claim 19 selected from the group consisting of:
1-(2-fluoro)phenyl-3-methyl-5-phenoxy-imidazolidine-2,4-dione,
1-(2,5-difluorophenyl)-3-methyl-5-phenoxy-imidazolidine-2,4-dione and
1-(2-fluoro-4-methyl)phenyl-3-methyl-5-phenoxy-imidazolidine-2,4-dione.

21. A method of controlling undesirable vegetation comprising applying to said vegetation or the locus thereof, an herbicidally effective amount of a compound having the formula

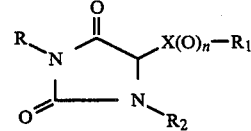

wherein

R is $C_1$-$C_3$ alkyl, phenyl or phenyl substituted with one or more alkyl, alkoxy, halo, haloalkyl or nitro;

$R_1$ is phenyl or phenyl substituted with one or more alkyl, alkoxy, halo, haloalkyl or nitro;

$R_2$ is lower alkyl, phenyl or phenyl substituted with one or more alkyl, halo or haloalkyl;

X is sulfur or oxygen; and n is an integer from 0 to 2.

22. The method of claim 21 wherein R is phenyl or phenyl substituted with one or more alkyl, alkoxy, halo, haloalkyl, nitro or combinations thereof.

23. The method of claim 21 wherein $R_2$ is $C_1$-$C_3$ alkyl.

24. The method of claim 21 wherein X is sulfur.

25. The method of claim 24 wherein n is the integer 0.

26. The method of claim 24 wherein n is 2.

27. The method of claim 21 wherein X is oxygen and n is the integer 0.

28. The method of claim 21 wherein R is $C_1$-$C_3$ alkyl.

29. The method of claim 23 wherein R is phenyl or phenyl substituted with one or more alkyl, alkoxy, halo, haloalkyl or nitro; $R_2$ is methyl; X is sulfur; and n is 0.

30. The method of claim 29 wherein the compound is selected from the group consisting of:

3-(2-fluorophenyl)-5-(phenylthio)-1-methylimidazolidine-2,4-dione,
3-(2-fluorophenyl)-5-(2-fluorophenylthio)-1-methylimidazolidine-2,4-dione,
3-(2-fluorophenyl)-5-(2-chlorophenylthio)-1-methylimidazole-2,4-dione,
3-(2-fluorophenyl)-5-(2-bromophenylthio)-1-methylimidazolidine-2,4-dione,
3-(2-fluorophenyl)-5-(2-isopropylphenylthio)-1-methylimidazolidine-2,4-dione,
3-(2-fluorophenyl)-5-(4-chlorophenylthio)-1-methylimidazolidine-2,4-dione,
3-(2-fluorophenyl)-5-(4-nitrophenylthio)-1-methylimidazolidine-2,4-dione,
5-(2-nitrothiophenoxy)-3-(2-fluorophenylthio)-1-methylimidazolidine-2,4-dione,
3-(2-fluorophenyl)-5-(2-methylphenylthio)-1-methylimidazolidine-2,4-dione,
3-(2-fluorophenyl)-5-(4-bromophenylthio)-1-methylimidazolidine-2,4-dione,
3-(2-fluorophenyl)-5-(2-methoxyphenylthio)-1-methylimidazolidine-2,4-dione,
3-(2,5-difluorophenyl)-5-(2-chlorophenylthio)-1-methylimidazolidine-2,4-dione,
3-(2,5-difluorophenyl)-5-(2-bromophenylthio)-1-methylimidazolidine-2,4-dione,
3-(2,5-difluorophenyl)-5-(4-chlorophenylthio)-1-methylimidazolidine-2,4-dione and
3-(2,5-difluorophenyl)-5-(2-bromophenylthio)-1-methylimidazolidine-2,4-dione.

31. The method of claim 22 wherein $R_1$ is phenyl or phenyl substituted with alkyl, alkoxy, halo, haloalkyl, nitro or combinations thereof; $R_2$ is $C_1$–$C_3$ lower alkyl; X is sulfur; and n is an integer from 0–2.

32. The method of claim 31 wherein n is the integer 2.

33. The method of claim 32 wherein the compound is 5-(4-fluorophenylsulfonyl)-3-(3-chlorophenyl)-1-methylimidazolidine-2,4-dione.

34. The method of claim 31 wherein $R_2$ is methyl.

35. The method of claim 28 wherein R is $C_1$–$C_3$ lower alkyl; $R_1$ is phenyl or phenyl substituted with alkyl, alkoxy, or halo; $R_2$ is phenyl, phenyl substituted with one or more alkyl, halo or haloalkyl; X is sulfur; and n is the integer 0.

36. The method of claim 35 wherein R is methyl.

37. The method of claim 28 wherein $R_1$ is phenyl or phenyl substituted with one or more alkyl, alkoxy or halo; and $R_2$ is phenyl or phenyl substituted with one or more alkyl, halo or haloalkyl.

38. The method of claim 35 wherein the compound is selected from the group consisting of:
1-(2-fluorophenyl)-5-(2-chlorophenyl)thio-3-methylimidazolidine-2,4-dione,
1-(2-fluorophenyl)-5-(2-bromophenyl)thio-3-methylimidazolidine-2,4-dione,
1-(2,5-difluorophenyl)-5-(2-chlorophenyl)thio-3-methylimidazolidine-2,4-dione and
1-(2-fluorophenyl)-5-phenylthio-3-methylimidazolidine-2,4-dione.

39. The method of claim 27 wherein R is phenyl substituted with one or more halo or alkyl; $R_1$ is phenyl or phenyl substituted with one or more halo or alkyl; $R_2$ is $C_1$–$C_3$ lower alkyl; X is oxygen and n is the integer 0.

40. The method of claim 39 wherein the compound is selected from the group consisting of:
1-(2-fluoro)phenyl-3-methyl-5-phenoxy-imidazolidine-2,4-dione,
1-(2,5-difluorophenyl)-3-methyl-5-phenoxy-imidazolidine-2,4-dione and
1-(2-fluoro-4-methyl)phenyl-3-methyl-5-phenoxy-imidazolidine-2,4-dione.

41. An herbicidal composition comprising:
(a) an herbicidally effective amount of a compound having the formula

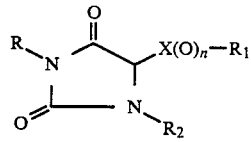

wherein
R is $C_1$–$C_3$ alkyl, phenyl or phenyl substituted with one or more alkyl, alkoxy, halo, haloalkyl or nitro;
$R_1$ is phenyl or phenyl substituted with one or more alkyl, alkoxy, halo, haloalkyl or nitro;
$R_2$ is lower alkyl, phenyl or phenyl substituted with one or more alkyl, halo or haloalkyl;
X is sulfur or oxygen; and
n is an integer from 0 to 2;
(b) an herbicidally suitable inert diluent or carrier.

42. An herbicidal composition according to claim 41 wherein R is phenyl or phenyl substituted with one or more alkyl, alkoxy, halo, haloalkyl, nitro or combinations thereof.

43. An herbicidal composition according to claim 41 wherein $R_2$ is $C_1$–$C_3$ alkyl.

44. An herbicidal composition according to claim 41 wherein X is sulfur.

45. An herbicidal composition according to claim 44 wherein n is the integer 0.

46. An herbicidal composition according to claim 44 wherein n is 2.

47. An herbicidal composition according to claim 41 wherein X is oxygen and n is the integer 0.

48. An herbicidal composition according to claim 41 wherein R is $C_1$–$C_3$ alkyl.

49. An herbicidal composition according to claim 43 wherein R is phenyl or phenyl substituted with one or more alkyl, alkoxy, halo, haloalkyl or nitro; $R_2$ is methyl; X is sulfur; and n is 0.

50. An herbicidal composition according to claim 49 wherein (a) is selected from the group consisting of:
3-(2-fluorophenyl)-5-(phenylthio)-1-methylimidazolidine-2,4-dione,
3-(2-fluorophenyl)-5-(2-fluorophenylthio)-1-methylimidazolidine-2,4-dione,
3-(2-fluorophenyl)-5-(2-chlorophenylthio)-1-methylimidazole-2,4-dione,
3-(2-fluorophenyl)-5-(2-bromophenylthio)-1-methylimidazolidine-2,4-dione,
3-(2-fluorophenyl)-5-(2-isopropylphenylthio)-1-methylimidazolidine-2,4-dione,
3-(2-fluorophenyl)-5-(4-chlorophenylthio)-1-methylimidazolidine-2,4-dione,
3-(2-fluorophenyl)-5-(4-nitrophenylthio)-1-methylimidazolidine-2,4-dione,
5-(2-nitrothiophenoxy)-3-(2-fluorophenylthio)-1-methylimidazolidine-2,4-dione,
3-(2-fluorophenyl)-5-(2-methylphenylthio)-1-methylimidazolidine-2,4-dione,
3-(2-fluorophenyl)-5-(4-bromophenylthio)-1-methylimidazolidine-2,4-dione, 3-(2-fluorophenyl)-5-(2-methoxyphenylthio)-1-methylimidazolidine-2,4-dione,
3-(2,5-difluorophenyl)-5-(2-chlorophenylthio)-1-methylimidazolidine-2,4-dione,
3-(2,5-difluorophenyl)-5-(2-bromophenylthio)-1-methylimidazolidine-2,4-dione,
3-(2,5-difluorophenyl)-5-(4-chlorophenylthio)-1-methylimidazolidine-2,4-dione and
3-(2,5-difluorophenyl)-5-(2-bromophenylthio)-1-methylimidazolidine-2,4-dione.

51. An herbicidal composition according to claim 43 wherein $R_1$ is phenyl or phenyl substituted with alkyl, alkoxy, halo, haloalkyl, nitro or combinations thereof; $R_2$ is $C_1$–$C_3$ lower alkyl; X is sulfur; and n is an integer from 0–2.

52. An herbicidal composition according to claim 51 wherein n is the integer 2.

53. An herbicidal composition according to claim 52 wherein (a) is the compound 5-(4-fluorophenylsulfonyl)-3-(3-chlorophenyl)-1-methylimidazolidine-2,4-dione.

54. An herbicidal composition according to claim 51 wherein $R_2$ is methyl.

55. An herbicidal composition according to claim 48 wherein R is $C_1$–$C_3$ lower alkyl; $R_1$ is phenyl or phenyl substituted with alkyl, alkoxy, or halo; $R_2$ is phenyl, phenyl substituted with one or more alkyl, halo or haloalkyl; X is sulfur; and n is the integer 0.

56. An herbicidal composition according to claim 55 wherein R is methyl.

57. An herbicidal composition according to claim 48 wherein $R_1$ is phenyl or phenyl substituted with one or more alkyl, alkoxy or halo; and $R_2$ is phenyl or phenyl substituted with one or more alkyl, halo or haloalkyl.

58. An herbicidal composition according to claim 55 wherein (a) is selected from the group consisting of:
1-(2-fluorophenyl)-5-(2-chlorophenyl)thio-3-methylimidazolidine-2,4-dione,
1-(2-fluorophenyl)-5-(2-bromophenyl)thio-3-methylimidazolidine-2,4-dione,
1-(2,5-difluorophenyl)-5-(2-chlorophenyl)thio-3-methylimidazolidine-2,4-dione and
1-(2-fluorophenyl)-5-phenylthio-3-methylimidazolidine-2,4-dione.

59. An herbicidal composition according to claim 47 wherein R is phenyl substituted with one or more halo or alkyl; $R_1$ is phenyl or phenyl substituted with one or more halo or alkyl; $R_2$ is $C_1$–$C_3$ lower alkyl; X is oxygen and n is the integer 0.

60. An herbicidal composition according to claim 59 wherein (a) is selected from the group consisting of:
1-(2-fluoro)phenyl-3-methyl-5-phenoxy-imidazolidine-2,4-dione,
1-(2,5-difluorophenyl)-3-methyl-5-phenoxy-imidazolidine-2,4-dione and
1-(2-fluoro-4-methyl)phenyl-3-methyl-5-phenoxy-imidazolidine-2,4-dione.

* * * * *